United States Patent

Tan et al.

[11] Patent Number: 6,114,373
[45] Date of Patent: Sep. 5, 2000

[54] N-ACETYL-5,6-DIMETHOXYTRYPTAMINE AND ITS FREE RADICAL SCAVENGING ACTIVITY

[76] Inventors: Dun-Xian Tan, 7458 Louis Pasteur #1202, San Antonio, Tex. 78229; Russel Joseph Reiter, 148 Garrapata, San Antonio, Tex. 78232; Mei-ting Yan, Jianshe 6 Road, Qing Cai Gong Suite 15, #102, Guangzhou, Guangton 510060, China

[21] Appl. No.: 09/217,405

[22] Filed: Dec. 21, 1998

[30] Foreign Application Priority Data

Mar. 18, 1998 [CN] China ............................. 98 1 13145.X

[51] Int. Cl.$^7$ .................. A61K 31/404; C07D 209/20; A01N 9/00; A01N 25/16; A01N 25/28
[52] U.S. Cl. .............................. 514/419; 548/496
[58] Field of Search .............................. 514/419; 548/496

[56] References Cited

U.S. PATENT DOCUMENTS

| | | | |
|---|---|---|---|
| 5,210,215 | 5/1993 | Politi et al. ............................. | 548/494 |
| 5,283,343 | 2/1994 | Dubocovich et al. .................. | 548/496 |
| 5,403,851 | 4/1995 | D'Orlando ............................. | 514/364 |
| 5,756,507 | 5/1998 | Goulet et al. ......................... | 514/255 |

OTHER PUBLICATIONS

CA 129: 302483 Melatonin Receptor Ligands: Synthesis . . . Study, Mor et al, 1998.
CA 127: 12976 1–(2–Alkanamidoethyl)–6–methoxyindole Derivatives: A . . . Analogs, Tarzia et al, 1997.

Primary Examiner—Floyd D. Higel

[57] ABSTRACT

The invention involves a novel chemical compound, N-acetyl-5,6-dimethoxytryptamine (compound I), which can also be defined as a melatonin derivative. The molecular weight of compound I is 262 and the chemical structure is as follows.

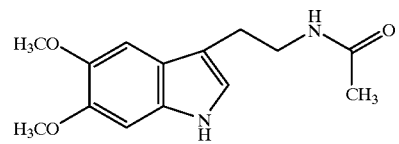

Compound I possesses potent in vitro and in vivo free radical scavenging capacity and exhibits protective effects against convulsions and brain damage induced by oxidative stress. It holds potential clinical usage for preventing and treating diseases which involve free radicals and oxidative stress.

7 Claims, 6 Drawing Sheets

N-ACETYL-5,6-DIMETHOXYTRYPTAMINE AND ITS FREE RADICAL SCAVENGING ACTIVITY

CROSS-REFERENCE TO RELATED APPLICATIONS

[11] Foreign Application Priority Data Aug. 26, 1998 [CN] China—1191219A
[51] Int. Cl6—C07D209/16
References Cited
U.S. Patent Documents
Class 548 Subclasses 496 and 497
U.S. Pat. No. 4,956,504—Takeuchi et al.
U.S. Pat. No. 5,053,424—Marzi et al.
U.S. Pat. No. 5,149,692—Doherty et al.
U.S. Pat. No. 5,210,215—Politi et al.
U.S. Pat. No. 5,283,343—Dubocovich et al.
U.S. Pat. No. 5,635,379—Deghenghi
U.S. Pat. No. 5,646,301—Deghenghi
6 CLAIMS, 6 DRAWING SHEETS

TECHENICAL FIELD

The present invention relates to a novel chemical compound (compound I), and the production and the potential clinical uses of said compound. Compound I is formed by substitution of a hydrogen atom at the 6 position of the indole ring in the melatonin molecule with a methoxy group. In the process of production, the starting material 5,6-dimethoxyindole is converted to compound I by 4 steps of conventional chemical reactions. Compound I is a potent novel free radical scavenger and antioxidant; therefore, it will be useful in preventing and treating diseases in which free radicals are part of the etiology.

BACKGROUND OF THE INVENTION

From its chemical structure, compound I can also be defined as a melatonin derivative or 6-methoxymelatonin. Melatonin is a main secretory product of pineal gland in vertebrates. The synthesis and secretion of melatonin shows a significant circadian rhythm and its production decreases with age. Thus, blood melatonin concentrations are 5–15 times higher at night than during the day and this circadian rhythms deteriorates with aging. Melatonin is a highly conserved molecule during evolution. It is found in most organisms from unicells to humans. Melatonin participates in several important physiological functions including the control of seasonal reproduction, improving immunological function, promoting sleeping, cancer inhibition and anti-aging. Recently, it was found that melatonin is a potent endogenous free radical scavenger (Tan et al., Endocrine J. 1: 57–60 1993). Melatonin may prolong the experimental animal life span up to 27% (Pierpaoli and Regelson, Proc. Natl. Acad. Sci. USA 91: 787–791 1994) and protect neurons against damage induced by a variety of oxidative stresses (Reiter, Prog. Neurobiol. 56: 356–384 1998). The action structure, in terms of free radical scavenging function, is attributed to the 5-methoxy group on the indole ring of melatonin (Tan et al., Endocrine J. 1: 57–60 1993). Direct free radical scavenging ability is a chemical reaction that does not require the molecule to interact with a receptor. When melatonin is used as a free radical scavenger, the receptor-mediated effects would produce side effects, for example, promoting steepness in the day time. Another disadvantage of melatonin is that a major portion of the melatonin in the circulation is quickly metabolized to 6-hydroxymelatonin and excreted into the urine. Melatonin's metabolism to 6-hydroxymelatonin occurs in the liver by a specific enzyme which converts the hydrogen atom at 6 position of indole ring in the melatonin molecule to a hydroxyl group. Thus, the biological half life of melatonin in the blood is short (about 20–40 min). The short biological half life of melatonin makes it less convenient for clinical use as a free radical scavenger (requiring repeated administration of melatonin to keep an effective blood concentration). In order to 1) enhance the free radical scavenging ability; 2) prolong the biological half life and 3) minimize the side effects of melatonin, compound I was designed by substituting the hydrogen atom at the 6 position of indole ring of melatonin with a methoxy group. The methoxy group possesses a p electron and it can share this p electron with the indole ring to form the p-π electron cloud. Once the hydrogen atom at the 6 position of the indole ring of melatonin is substituted with a methoxy group, the intensity of electron cloud on the indole ring is increased and so the free radical scavenging ability correspondingly increases for compound I. Because 6 position of the indole ring in melatonin molecule is occupied by a much larger methoxy group (compared with the hydrogen atom) in compound I the metabolic action of the sterol specific enzyme in the liver is blocked and the degradation rate for compound I is decreased markedly. In this way the biological half life of compound I will be much longer than that of melatonin. Furthermore, the structural change in compound I reduces its binding affinity to the membrane melatonin receptors thereby reducing the side effects of the molecule. To identify these advantages generated by the structural change which were designed by the inventors, both in vitro and in vivo experiments have been employed to test the free radical scavenging activity of compound I. The experimental results proved the prediction.

BRIEF SUMMARY OF THE INVENTION

It has now been found, which forms the object of the present invention, that the melatonin derivative, N-acetyl-5,6-dimethoxytryptamine (compound I), obtained by substitution of a hydrogen atom with a methoxy group at position 6 in the indole ring of melatonin molecule possesses potent oxygen free radical scavenging ability and neuronal protective effects in a manner even more efficacious than melatonin.

The present invention involves a processes of production of said compound, which includes starting with 5,6-dimethoxyindole; through 4 steps of chemical reactions the 5,6-dimethoxyindole is converted to said compound.

A further objective of the present invention is the pharmacological use of said compound in preventing and treating neurodegenerative diseases, heart diseases, cancer and other conditions which are believed to involve oxygen free radical damage in their etiology.

DETAILED DESCRIPTION OF THE INVENTION

Figure 1:
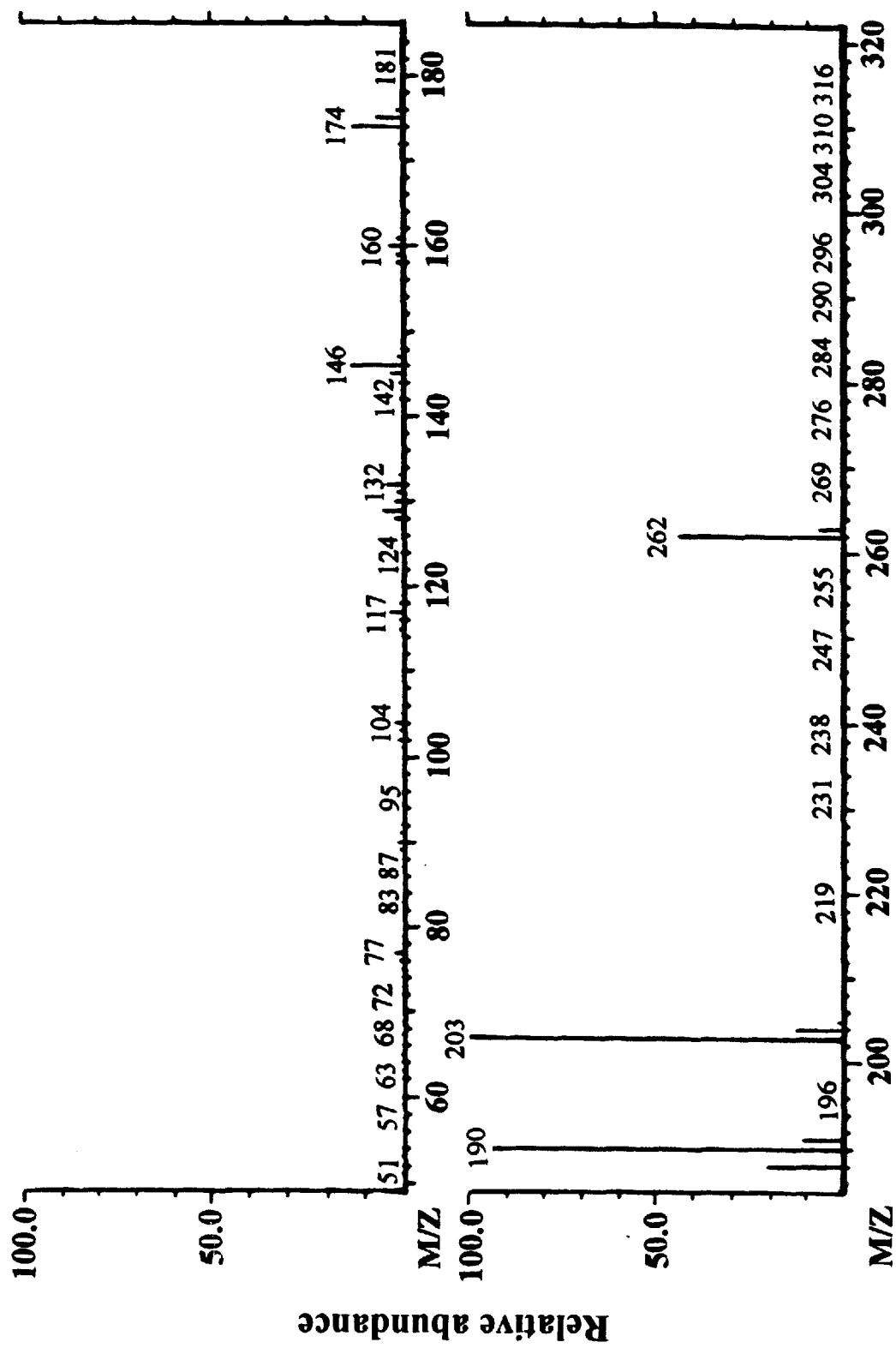
FIG. 1. The electron ionizing (EI) mass spectrum of compound I. The spectrum shows the melecular weight of compound I is 262.

It is extremely difficult to directly substitute the hydrogen atom at the position 6 of the indole ring in the melatonin molecule with a methoxy group. Due to the spatial effect and chemical reaction order, this substitution will more likely occur at position 3, 2 or 7 of the melatonin molecule. To overcome this difficult, the present invention employed 5,6-dimethoxyindole as the starting material to synthesize compound I. The production process consisted of 4 steps of conventional chemical reactions.

EXAMPLE 1

The Preparation of N-acetyl-5, 6-dimethoxytryptamine
Step 1. The synthesis of 3-diethyl-N-methyl-5,6-dimethoxyindole:

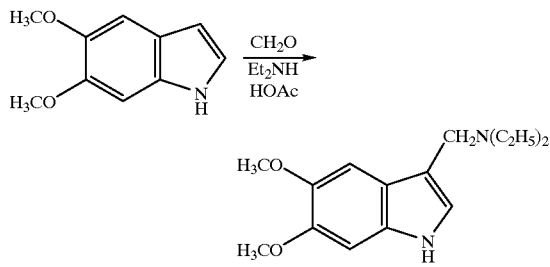

A solution of 1.4 ml of 60% HOAc and 0.48 gram (6.6 mmol) of Et2NH was prepared and cooled to about 5° C. To this solution was added 0.51 ml of formalin (37%). After stirring for 10 min at 5° C., this solution was poured into a chilled solution (15° C.) of 1 g (5.65 mmol) of 5,6-dimethoxyindole in 2 ml of EtOH. The resulting solution was allowed to warm to room temperature and then stirred for 1 h. The mixture was then poured into 20 ml of cold 1 N NaOH and extracted with three portions of $Et_2O$. The extracts were washed with NaCl solution. After drying over $Na_2SO4$, the $Et_2O$ was evaporated, leaving the 3-diethy-N-methyl-5,6dimethoxyindole as a viscous oil.

Step 2. The synthesis of 5,6-dimethoxy-3-indoleacetonitrile:

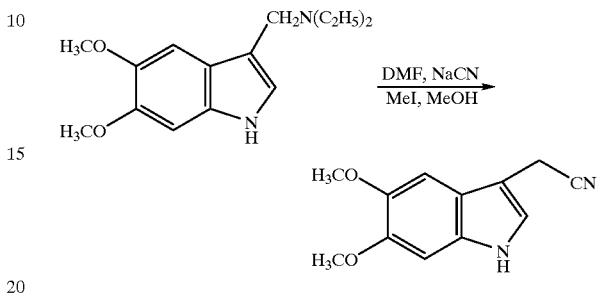

The crude 3-diethy-N-methyl-5,6-dimethoxyindole was taken up in a solution of 2 ml of MeOH, 1 ml of DMF, 1 ml of H2O and 1.33 g (2.7 mmol) of NaCN. A dropwise addition of 2.1 ml (4.8 g, 3.4 mmol) of MeI was then added over a period of 1 h. After stirring for a second hour, the mixture was poured into a 400 ml cold $H_2O$ and extracted with $CH_2Cl_2$. The extract were washed with $H_2O$ and dried over $Na_2SO_4$. The solvent was removed under vacuum, and the residue was recrystallized from benzene-hexane. The yield of 5,6-dimethoxy-3-indoleacetonitrile was 0.5 g (50% based on 5,6-dimethoxyindole).

Step 3. The synthesis of 5,6-dimethoxytryptamine

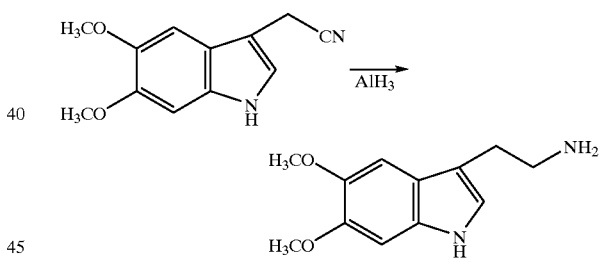

A solution of $AlH_3$ in THF was prepared by dropwise addition of a solution of 0.52 ml (0.98 g, 10 mmol) of 100% $H_2SO_4$ in 4 ml of THF to a mixture of 0.76 g (20 mmol) of LiAlH4 and 20 ml of THF. Without removing the precipitated $Li_2SO_4$, a solution of 0.5 g (2.33 mmol) of 5,6-dimethoxy-3-indoleacetonitrile in 4 ml of THF was added over 30 min period. after stirring for another hour, the excess hydride was destroyed by the addition of small chips of ice. Most of the supernatant THF solution was decanted (setting aside most of the THF at this point greatly reduces emulsion formation in the subsequent extraction). The precipitated aluminum salts were treated with cold 20% NaOH, and the resulting cloudy solution was extracted with $CHCl_3$. These extracts were combined with the THF solution, washed with NaCl solution, and dried over $Na_2SO_4$. The solvents were removed, and the residue was triturated with Et2-pentane. The crystalline product was washed with hot Et₂O-Skelly B and dried, giving 0.44 g (83%) of pure 5,6-dimethoxytryptamine.

Step 4. The systhesis of N-acetyl-5,6-dimethoxytryptamine:

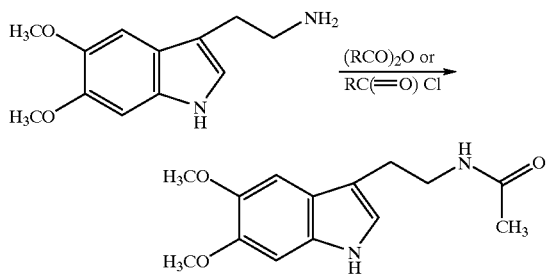

A solution of 0.44 g (2.028 mmol) of 5,6-dimethoxytryptamine in 3.2 ml of $C_6H_6$ and 0.8 ml of pyridine cooled with ice, as 0.4 ml of $Ac_2O$ was added. The ice bath was removed and the solution stirred for 3 h. The volatile metarials then were removed under vacuum. The residue was taken up in CHCl3 and washed with 5% $NaHCO_4$ solution followed by saturated NaCl solution. After dry over $Na_2SO_4$, the sovent was evaporated and product was recrystallized from $C_6H_6$. The yield of N-acetyl, 5,6 dimethoxytryptamine is 0.40 g (91%).

Figure 2:
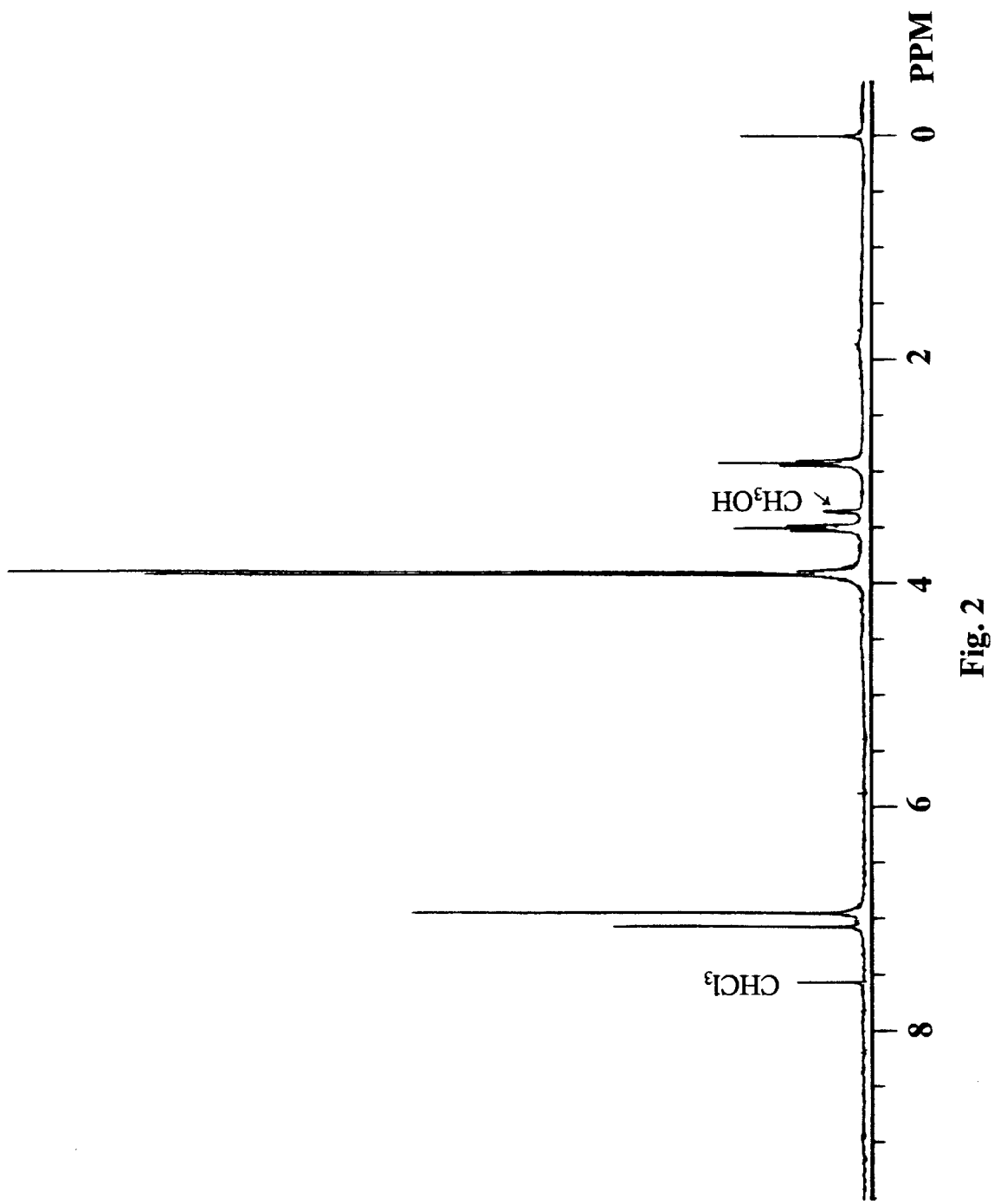
FIG. 2. A. $^1$H NMR spectrum of compound I in $CDCl_3$:$CD_3OD$ 1 solution obtained at 350 MHz.

The final product was analysed using mass spectrometry (MS) and proton nuclear magnetic resonance ($^1$HNMR). The MS and $^1$HNMR analysis confirmed the final product is highly pure N-acetyl-5,6-dimethoxytryptamine (FIGS. 1 and 2).

EXAMPLE 2
The In Vitro Experiment to Test the Free Radical Scavenging Ability of N-acetyl-5,6-Dimethoxytryptamine.

The hydroxyl radical (HO˙) is the most reactive and cytotoxic species among free radicals. It is believed to be involved in the etiology of many diseases including aging, Alzheimer disease, Parkinson disease, heart disease and cancer (Lubec, J. Invest. Med. 44: 324–346 1996). Because of its high reactivity, HO˙ once formed either in vitro or in vivo lasts for a very short time (half life about $10^{-9}$ s) and, therefore, HO˙ cannot be measured directly. However, by using a spin trapping agent, in this case 5,5-dimethylpyrroline-N-oxide (DMPO), an adduct (DMPO-HO˙) is formed between the spin trapping agent and the HO˙. The adducts have a longer half life and therefore they can be more readily quantified. To investigate whether compound I possesses HO˙ scavenging activity the photolysis of hydrogen peroxide by ultraviolet (UV) light was employed to generate HO˙ (Towel et al., Anal. Biochem. 196: 111–119 1991).

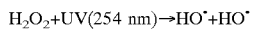

When DMPO is incubated in this system the DMPO will traps the HO˙ to form a relatively stable DMPO- HO˙ adduct.

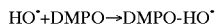

In the present study, the DMPO-HO˙ adduct was detected by an electro-chemical (EC) detector attached to a high performance liquid chromatography (HPLC) system. The system was comprised of a Water 501 pupm with Water 604 EC detector connected to an HP 3396 series II integrator and a microsorb-MV 5 μm octyl (15 cm×4.6 mm) analytic column. The mobile phase was composed of 0.03 M citric acid, 0.05 M sodium acetate and 15% acetonitrile, pH 5.1 at a flow rate of 1 ml per min. The applied potential was 1.0 volt and volume of the injected sample was 20 μl. The different concentrations of compound I were tested in this system and its efficacy in scavenging the HO˙ was compared with that of melatonin.

Figure 3:
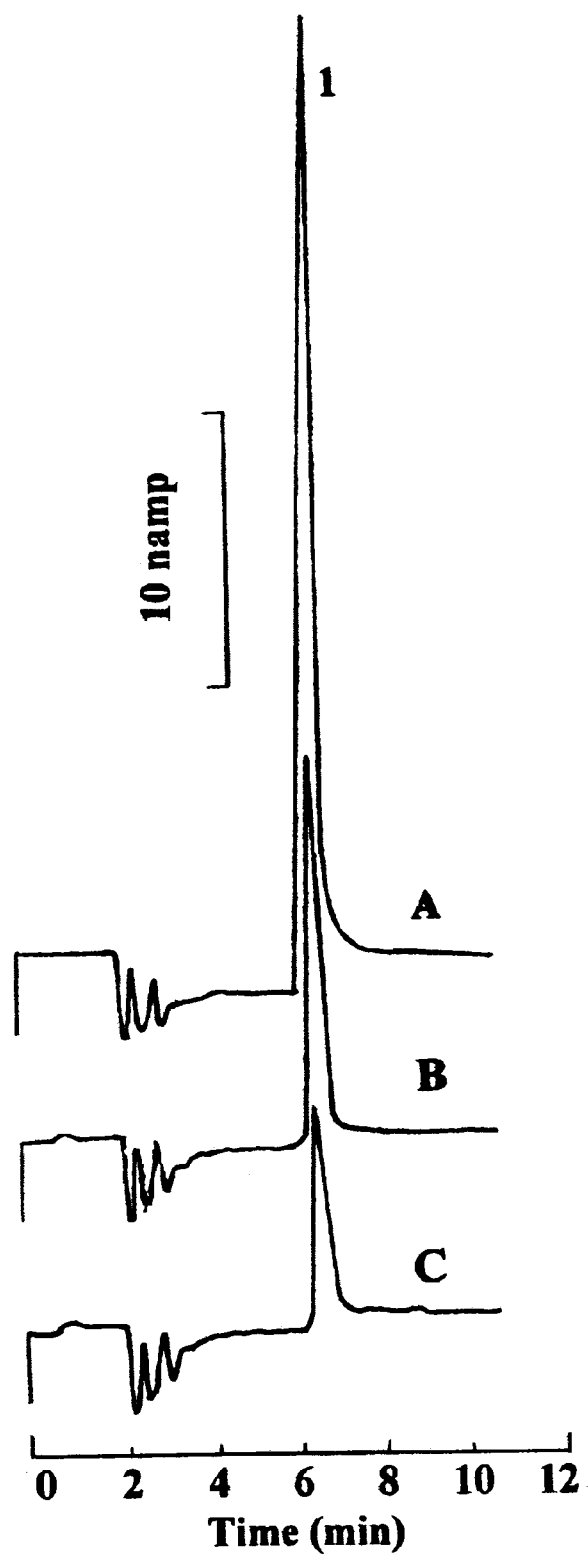
FIG. 3. Effect of compound I and melatonin on the formation of DMPO-HO· adducts as measured by an HPLC-EC. trace (A): DMPO alone incubated in HO· generation system; trace (B): DMPO plus melatonin incubated in HO· generation system; trace (C): DMPO plus compound I incubated in HO˙ generation system. Peak 1 is the signal produced by the DMPO-HO˙.
Figure 4:
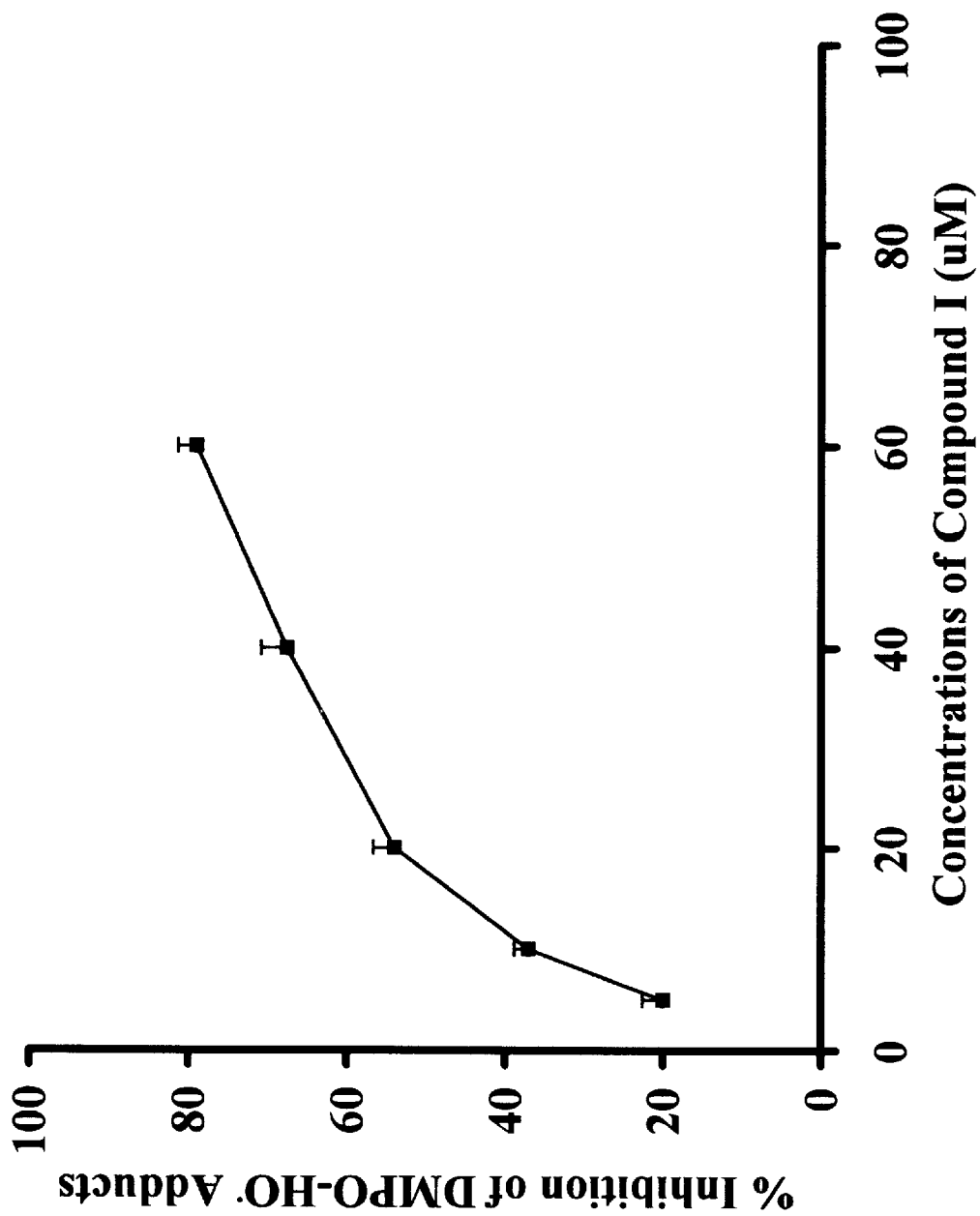
FIG. 4. Dose-response inhibition of DMPO-HO˙ adduct formation using by compound I. The DMPO-HO˙ adducts were detected by HPLC-EC. The data show means+SE for six separate experiments.

The results show that compound I can effectively suppress DMPO-HO˙ adduct formation and its efficacy is greater than that of melatonin (FIG. 3) and this suppression is in a dose-response relationship (FIG. 4). The IC50 (concentration required to produce 50% inhibition of the DMPO-HO˙ formation) of compound I was 15 μM which was lower than that of melatonin (21 μM (Tan et al., Endocrine J. 1: 57–60 1993). The results indicate that compound I is a potent novel HO˙ scavenger.

EXAMPLE 3
The In Vivo Experiments to Test the Free Radical Scavenging Effect of Compound I:

Kainic acid (KA) was employed to test the in vivo free radical scavenging and antioxidant activities of compound I. KA is an excitatory neurotoxin which destroys neuronal cells by free radical generation (Coyle and Schwarcz, Nature 263: 244–246 1976). Male CD2-FI mice (26–30 g) were chosen as the experimental subject. The mice were housed in windowless room with automatically regulated temperature 22±2° C. and 14 h light/10 h dark cycle. The mice received standard laboratory chow and water ad libitum. The mice were randomized into 4 groups. Group 1 (7 mice) received vehicle (0.9% NaCl solution); Group 2 (15 mice) received a subcutaneous injection of KA at a dose of 40 mg/kg; Group 3 (15 mice) received a subcutaneous injection of KA of 40 mg/kg plus compound I at a dose of 5 mg/kg; Group 4 (15 mice) received a subcutaneous injection of KA (40 mg/kg) plus melatonin at a dose of 5 mg/kg. Compound I and melatonin were administered intraperitoneally 10 min before KA injection.

The Neuro Behavioral Observation:

Immediately following the injections, neurobehavioral changes were monitored. The observation period extended for 4 hours following the injections. The death rate at 48 hours was recorded. Mice that received the vehicle injection did not show any visible neurobehavioral changes and all of them survived. By contrast, all of the mice that received KA developed some neurobehavioral changes including arching of tail, tremors and seizures. The death rate in this group was 33%. In the KA plus melatonin treated mice, the incidence of tail arching decreased to 33% (p=0.009) as compared to 86% in the KA-treated mice. Tremors and seizures decreased from 100% in the KA-treated mice to 40% (p=0.001), respectively, and the death rate was reduced to 20%. However, in KA plus compound I treated mice, none of them died and the incidence of seizures was further reduced to 20%. The protective effects of compound I on death and seizures induced by KA are obviously more benificial than melatonin. All of the data were listed in table 1.

TABLE 1

Effects of compound I and melatonin on KA-induced neurobehavioral activities and death in mice.

| Group | n | Tail arch | Tremors | Seizures | Death |
|---|---|---|---|---|---|
| | | | Incidence (%) | | |
| Control | 7 | 0 | 0 | 0 | 0 |
| KA | 15 | 86 | 100 | 100 | 33 |

TABLE 1-continued

Effects of compound I and melatonin on KA-induced neurobehavioral activities and death in mice.

| Group | n | Tail arch | Tremors | Seizures | Death |
|---|---|---|---|---|---|
| KA + Compound I | 15 | 40** | 40** | 20**+ | 0*+ |
| KA + Melatonin | 15 | 33** | 40** | 40** | 20 |

KA, kainic acid.
*$p < 0.05$;
**$p < 0.001$ vs KA,
+$p < 0.05$ vs Melatonin.

Figure 5:
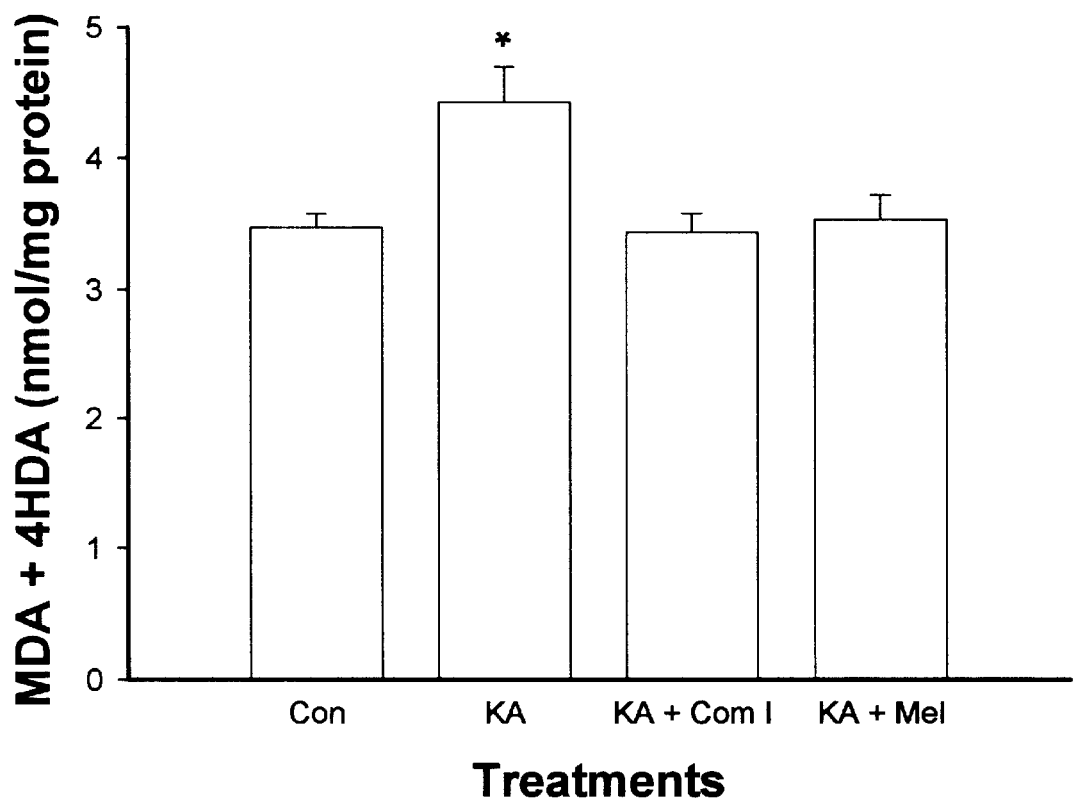
FIG. 5. Effect of melatonin on brain lipid proxidation in mice treated with kainic acid. Lipid proxidation is expressed as MDA+4-HDA per mg protein. Data are expressed as means ±SE; n=5. KA=kainic acid; Mel=melatonin; * $p<0.05$, KA group vs other groups.

The Brain Oxidative Damage Test:

Forty-eight hours after treatment, 5 mice of each group were sacrificed and the cerebral cortex was excised and immediately placed on dry ice and stored at $-80°$ C. for the lipid prooxidation product (LPO) assay. LPO is the most commonly used index of free radical damage and the assay used to measure the level of LPO is described in a kit avaliable from Calbiochem (LA Jolla, Calif.). LPO was expressed as malondialdehyde (MDA) and 4-hydroxyalkenals (4-HDA)/mg protein. The level of LPO in the cerebral cortex of mice in the control group was $3.47=0.18$ nmol/mg protein; in KA injected mice the level of LPO was increased to $4.42=0.11$ nmol/mg protein. This increase, when compared to the control mice, was great than 27% ($p<0.05$). In the KA+compound I and KA+melatonin treated mice the level of LPO in brain was reduced to control levels (FIG. 5). Thus, compound I as well as melatonin reduced the level of oxidative damage to the brain induced by the neurotoxin KA.

Figure 6:
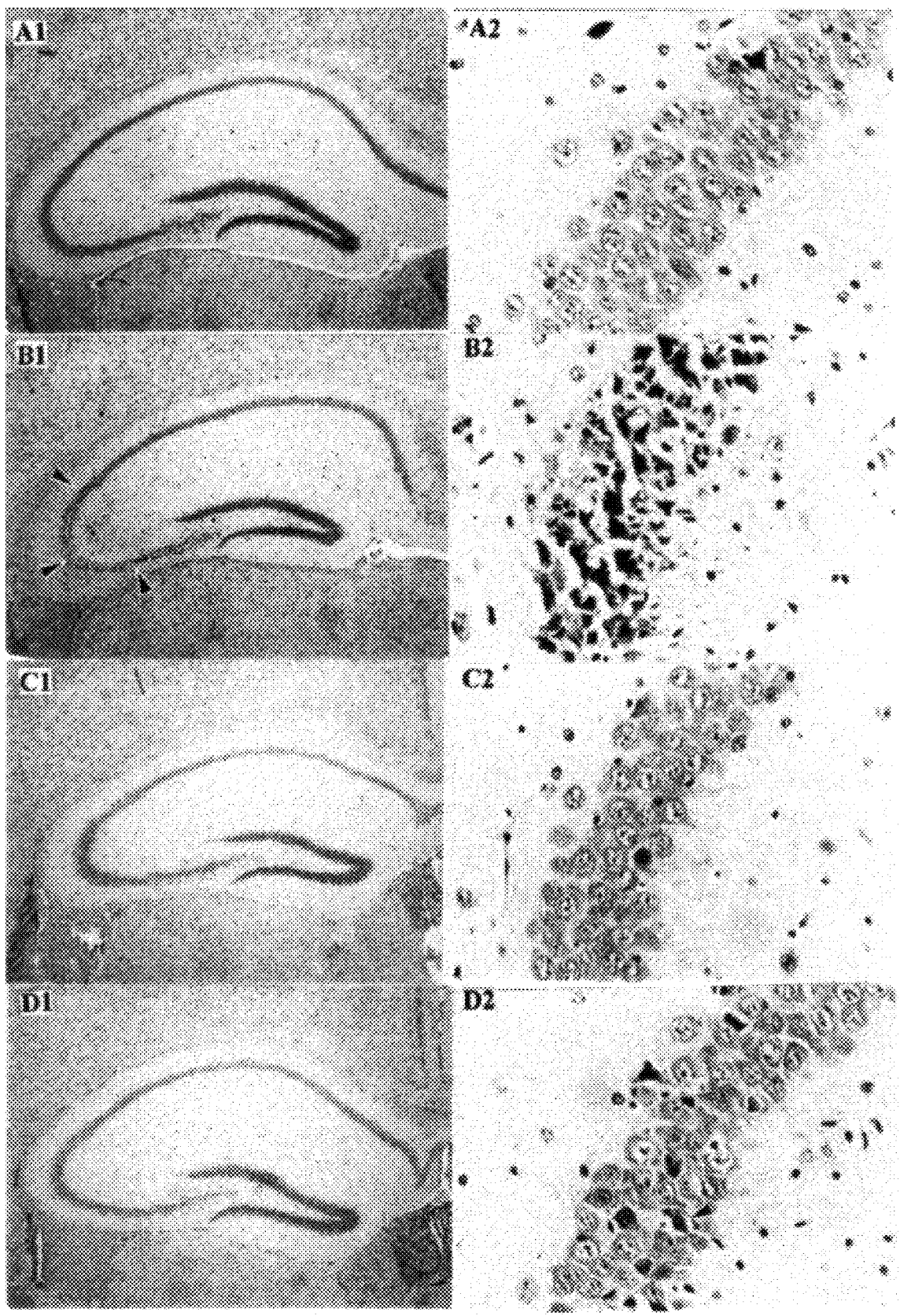
FIG. 6. Protective effect of compound I and melatonin against KA-induced morphological changes in the hippocampus of the mouse brain. A1 and A2 are photographs of the hippocampus of a control mouse brain. A1 is an overview photograph while A2 shows the details of pyramidal neurons in the hippocampal CA3 subregion of mouse brain. In these micrographs the pyramidal neurons of the hippocampus proper appear normal and the bulk of the pyramidal neurons appear functional. B1 and B2 show the hippocampus of a mouse brain treated with KA. The arrow heads (B1) identify the area where the pyramidal neurons are damaged. The morphological architecture of neurons in the hippocampal CA3 region were destroyed. Under high power magnification (B2), the neuronal membranes are difficult to identify, the nuclei are pyknotic and virtually all neurons appear to be in a state of degeneration. C1, C2 and D1, D2 are photomicrographs of the hippocampi of mice brains treated with KA plus compound I and KA plus melatonin, repectively. The neurons in these photographs appear similar to those in A1 and A2. No obviously neuronal damage is observed.

The Morphological Observations:

Seven days following the treatment, representative mice in each of the groups mentioned above were sacrificed. The brains were immersed in normal fixation buffer. The hippocampi and surrounding tissue were dissected from the whole brain, cut and stained with hematoxylin and eosin. The morphological assessment of neuronal damage was determined by using light microscopy. In the brains of control mice no visible neuronal damage was observed. By contrast, in the brains of mice treated with KA the pyramidal neurons of the hippocampus were severely damaged. The induced neuronal damage was concentrated in the hippocampal CA3 area. The total histological architecture of CA3 area was altered. Virtually all of the pyrimadal neurons in this area were destroyed. The cell membranes appeared to have disintegrated and the nuclei of the cells were condensed and pyknotic. These changes are consistent with cell death. On the other hand, in KA plus compound I and KA plus melatonin treated mice, the hippocampal CA3 area of the brain was still intact. Few damaged neurons were observed microcopically in this area in these two groups (FIG. 6). The results show that the compound I possesses significant potential as a protective agent against the neuronal damage induced by oxidative stress.

Since aging processes, heart disease, cancer and neurodegenerative diseases including Alzheimer disease and Parkinson disease are believed to involve free radical damage, many free radical scavengers and antioxidants, for example, vitamin E, vitamin C, β-carotine are used to retard, prevent and treat these processes and diseases. The potent and novel free radical scavenger, compound I, possesses a potential clinical use for prevention and treatment of these diseases and other free radical related diseases in humans.

What is claimed is:

1. A method of treating a free radical-related disease which comprises administering to a mammal a pharmaceutical composition of 6-methoxymelatonin.

2. A method according to claim 1 wherein the free radical-related disease is a neurodegenerative disease.

3. A method according to claim 1 wherein the free radical-related disease is Alzheimer's disease or Parkinson's disease.

4. A method according to claim 1 wherein the free radical-related disease is convulsions.

5. A method according to claim 1 wherein the free radical-related disease is the retardation of the aging processes.

6. A method according to claim 1 wherein the free radical-related disease is heart disease.

7. A method according to claim 1 wherein the free radical-related disease is cancer.

* * * * *